(12) United States Patent
Lee

(10) Patent No.: US 6,554,835 B1
(45) Date of Patent: Apr. 29, 2003

(54) SKULL FIXATION DEVICE

(76) Inventor: Ming-Kung Lee, 4F, 13, 2 Alley, Lane 31, An-Kang Road, Hsin-Tien City, Taipei Hsien (TW)

( * ) Notice: Subject to any disclaimer, the term of this patent is extended or adjusted under 35 U.S.C. 154(b) by 300 days.

(21) Appl. No.: 09/640,998

(22) Filed: Aug. 18, 2000

(30) Foreign Application Priority Data

Dec. 8, 1999 (TW) ........................................ 88220914 U

(51) Int. Cl.$^7$ ............................................... A61B 17/56
(52) U.S. Cl. .......................... 606/72; 606/151; 606/69
(58) Field of Search .......................... 606/72, 205, 232, 606/69, 129, 213, 53, 75, 104, 74, 73, 151; 24/297, 324, 662, 703.1; 411/61, 548, 447, 967; 132/276, 280

(56) References Cited

U.S. PATENT DOCUMENTS

| | | | | |
|---|---|---|---|---|
| 721,070 A | * | 2/1903 | McGill | ........................ 132/276 |
| 1,817,584 A | * | 8/1931 | Rosenberg | .................... 411/61 |
| 2,748,645 A | * | 6/1956 | Peckham et al. | .......... 24/703.1 |
| 6,190,389 B1 | * | 2/2001 | Wellisz et al. | ................ 606/69 |
| 6,197,037 B1 | * | 3/2001 | Hair | ............................ 606/151 |
| 6,258,091 B1 | * | 7/2001 | Sevrain et al. | ............... 606/213 |
| 6,293,956 B1 | * | 9/2001 | Crainich et al. | ............. 606/151 |
| 6,302,884 B1 | * | 10/2001 | Wellisz et al. | ................ 606/69 |

* cited by examiner

Primary Examiner—Pedro Philogene
(74) Attorney, Agent, or Firm—Bacon & Thomas, PLLC

(57) ABSTRACT

A skull fixation device. The device includes a clamp top portion, two clamp rods connected with the clamp top portion, and two bottom clamp legs connected with the two clamp rods. The two clamp rods are substantially coplanar such that the two clamp rods form an angle ranging between 30° and 150°. An imaginary surface formed by the coplanar two clamp rods is substantially perpendicular to the clamp top portion.

7 Claims, 7 Drawing Sheets

SKULL FIXATION DEVICE

FIELD OF THE INVENTION

The present invention relates to a skull fixation device.

BACKGROUND OF THE INVENTION

In the conventional surgical operation of the human skull, the wire and the craniotomy pin are used to fix the skull. For example, U.S. Pat. No. 5,549,620 discloses a skull fixation device comprising an upper block, a lower block, and a clamp rod. Such a prior art skull fixation device as described above is defective in design in that the skull must be provided with a round hole to facilitate the disposing of the skull fixation device, thereby resulting in the prolongation of the surgical operation as well as the post-surgical healing process.

SUMMARY OF THE INVENTION

It is the primary objective of the present invention to provide a skull fixation device which is free from the deficiencies of the skull fixation device of the prior art described above.

It is another objective of the present invention to provide a skull fixation device having an elasticity.

The skull fixation device of the present invention is in fact a fixation clamp which is used to fix a skull without having to drill a round hole in the skull, thereby shortening the duration of the surgical operation. In view of the skull fixation device of the present invention being elastic, providing freedom of slight vibration to the skull being clamped, the post-surgical healing process is accelerated.

DETAILED DESCRIPTION OF THE EMBODIMENTS

The skull fixation device of the present invention comprises a clamp top portion, two clamp rods, and two bottom clamp legs. The two clamp rods are connected with the clamp top portion and the two bottom clamp legs.

The present invention is characterized by the two clamp rods which are substantially coplanar such that they form an angle ranging between 30° and 150°. The planar surface formed by the two clamp rods is substantially perpendicular to the clamp top portion.

The clamp top portion and the two clamp rods are connected in such a manner that they are preferably made integrally. In the same way, the two clamp rods and the two bottom clamp legs are connected such that they are made integrally. Preferably, the skull fixation device of the present invention is formed integrally of an elastic linear body which has a substantially round cross section.

Figure 1A:
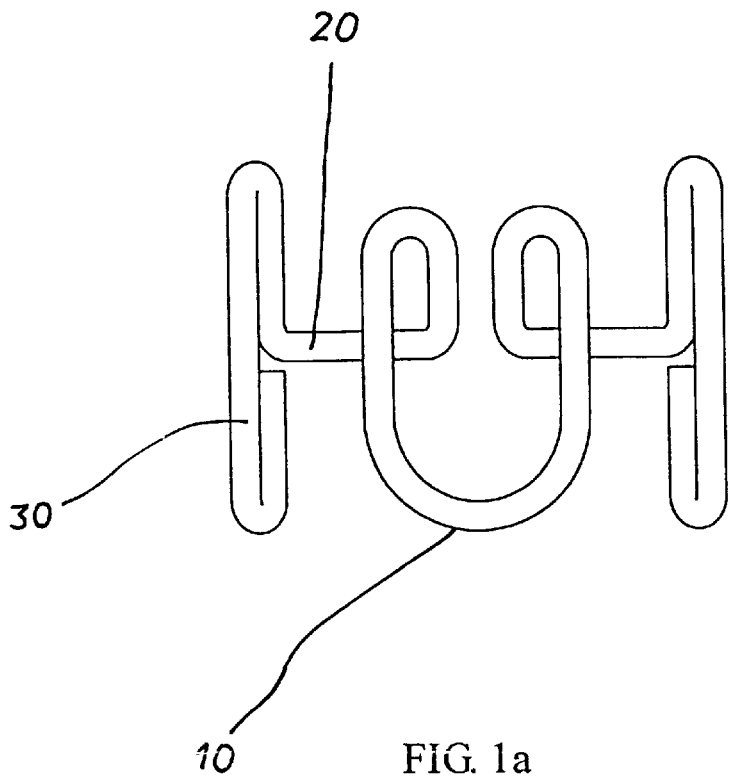
FIGS. 1a–1d are respectively a top view, a perspective view, a rear view, and a side view of a skull fixation device of a preferred embodiment of the present invention.

The clamp top portion of the present invention is similar in shape to any prior art clamp top portion. As shown in FIG. 1a, the clamp top portion has an opening annular H shape.

Preferably, the clamp rod is a round elastic thread having a diameter substantially equal to the width of the cut slot of the skull-opening surgery.

The two clamp rods form an angle ranging between 30° and 150°, preferably between 60° and 120°, more preferably between 75° and 105°. The best angle is 90°. The line dividing equally the angle formed by the two clamp rods is substantially and preferably perpendicular to the planar surface of the clamp top portion.

Preferably, the two bottom clamp legs and the two clamp rods are substantially normal to one another.

Preferably, the shortest distances between the clamp top portion and the two bottom clamp legs are substantially on a par with each other. Preferably, the shortest distance is substantially equal to or smaller than the thickness of the skull.

The skull fixation device of the present invention is made of any biologically-compatible elastic material, such as a metal wire made of titanium, titanium alloy, stainless steel, etc.

The preferred embodiment of the present invention is described hereinafter with reference to the accompanying drawings.

Figure 1B:
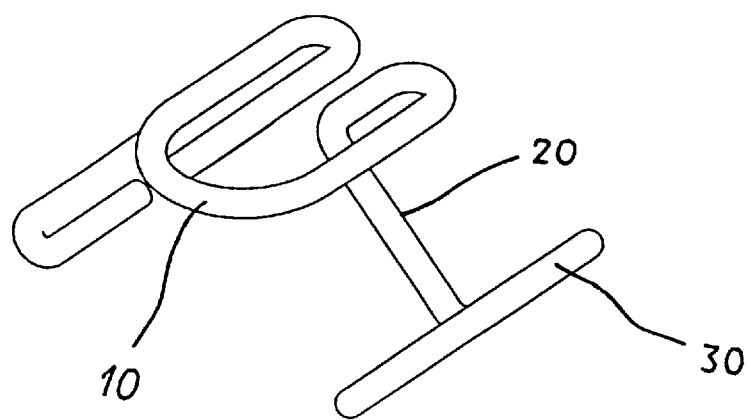
Figure 1C:
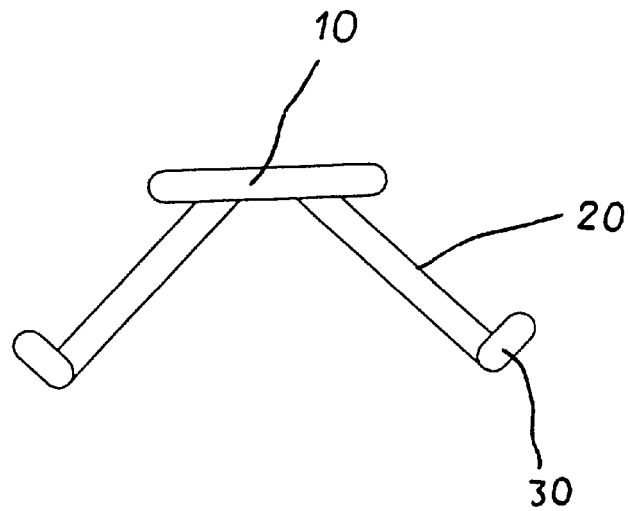
Figure 1D:
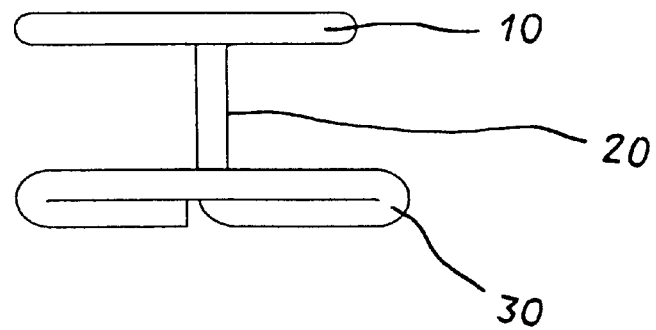

As shown is FIGS. 1a–1d, the reference numerals of the clamp top portion, the clamp rod and the bottom clamp leg are 10, 20, and 30 respectively. The two clamp rods 20 form an angle of 90°. The two clamp rods 20 and the clamp top portion 10 form separately an angle of 45°, as shown in FIG. 1C. The two clamp rods 20 form a planar surface which forms with the clamp top portion 10 an angle of 90°, as shown in FIG. 1d. The two bottom clamp legs 30 and the two clamp rods 20 form separately an angle of 90°, as shown in FIGS. 1a, 1b, and 1d.

Figure 2A:
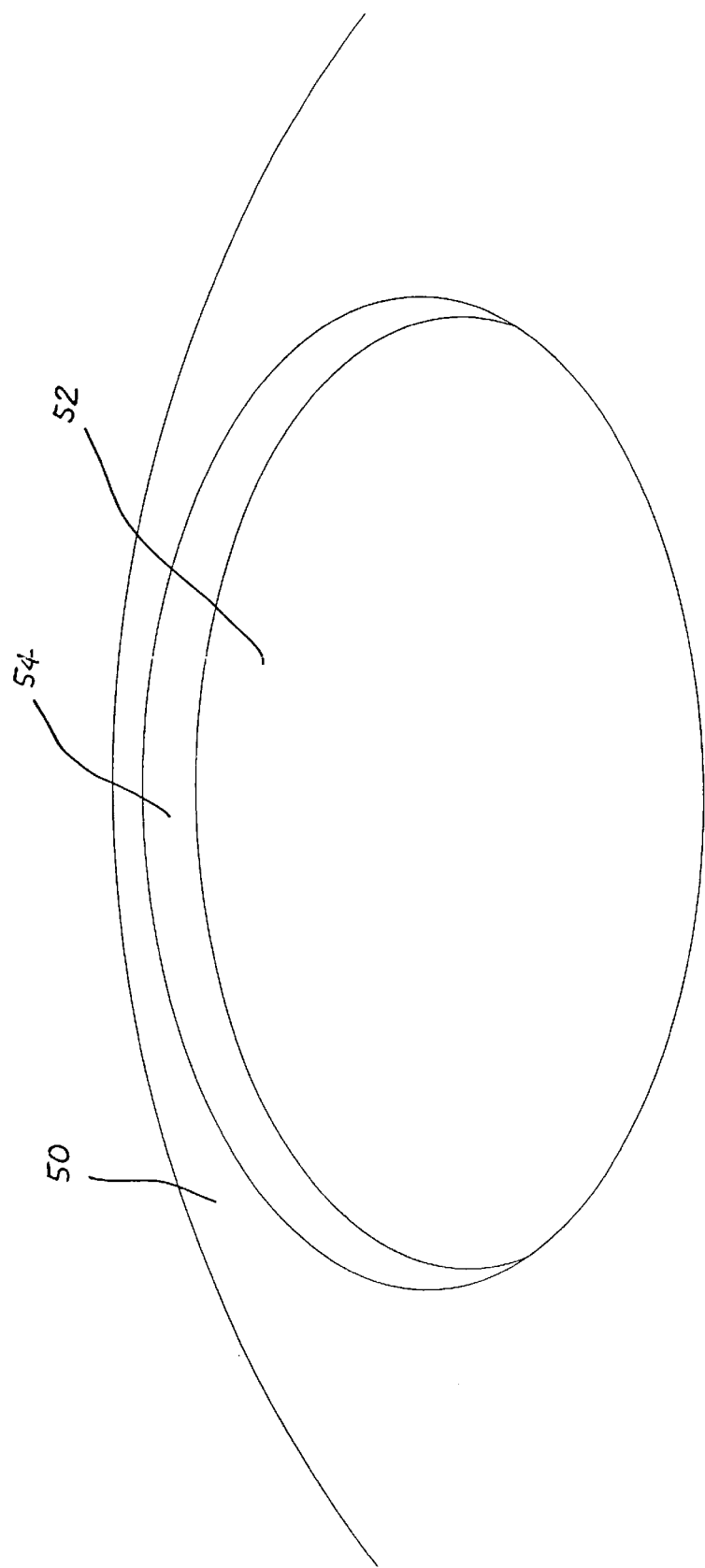
FIGS. 2a–2e are sequential schematic views of the surgical operation using the skull fixation device of the preferred embodiment of the present invention.
Figure 2B:
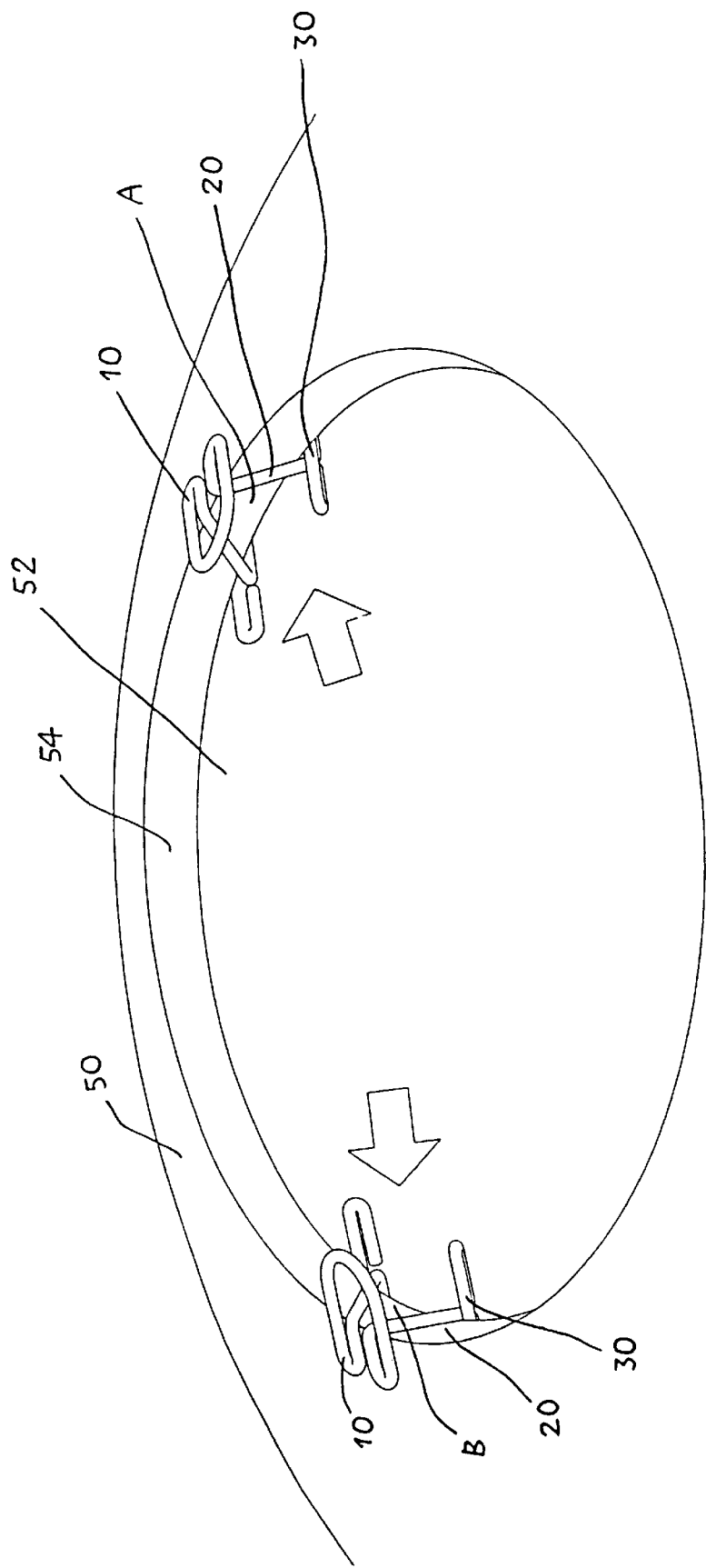
Figure 2C:
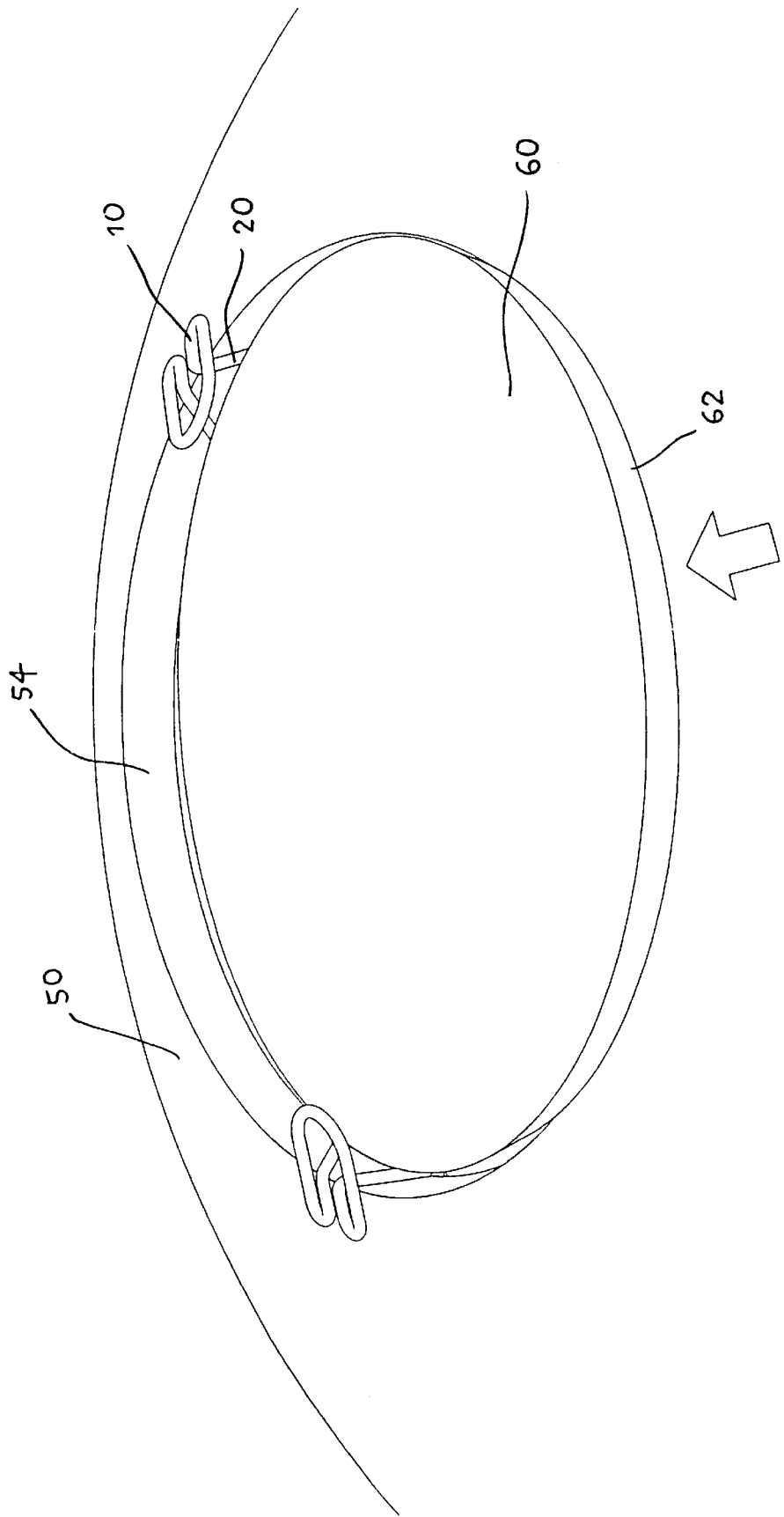
Figure 2D:
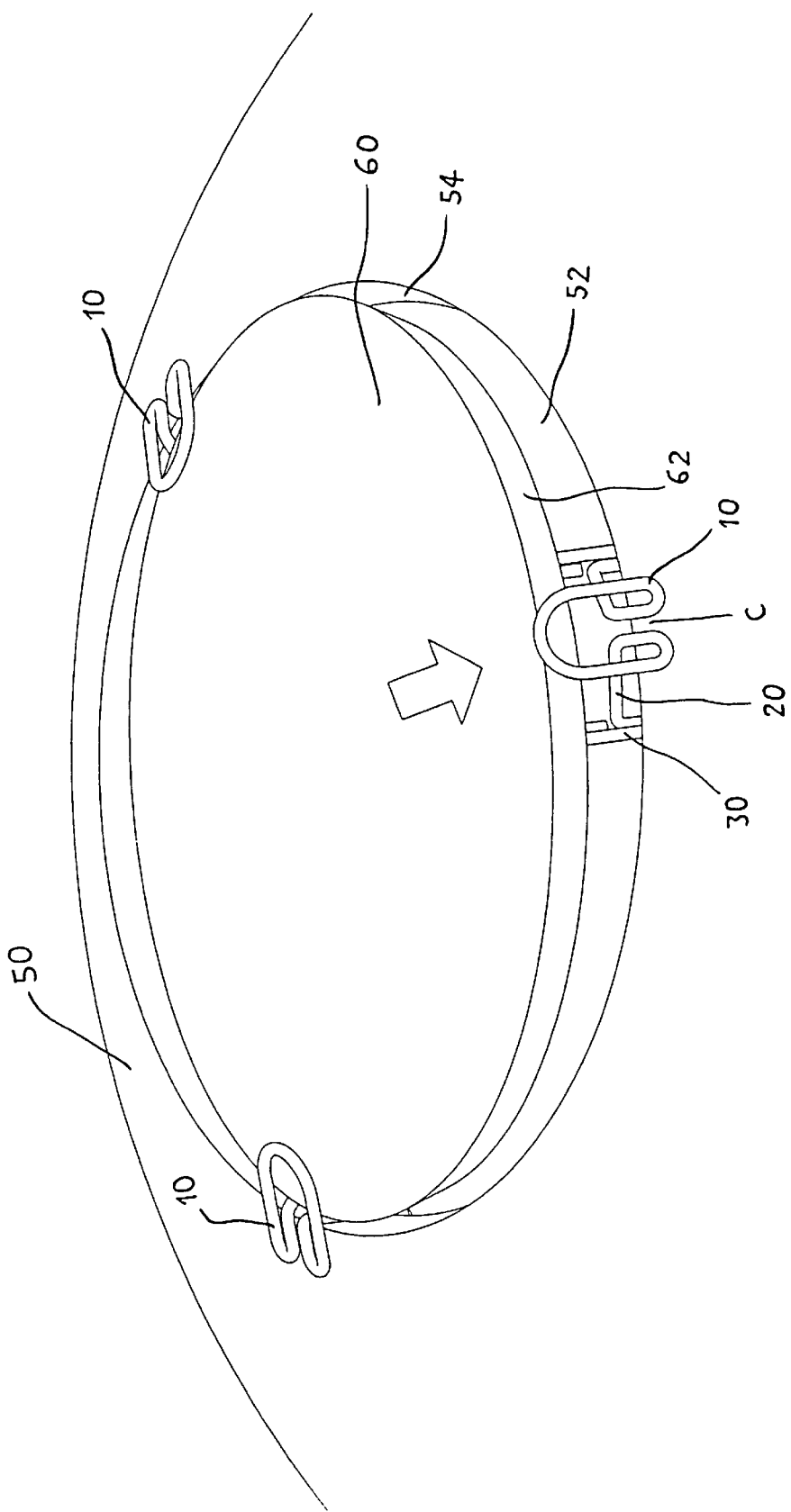
Figure 2E:
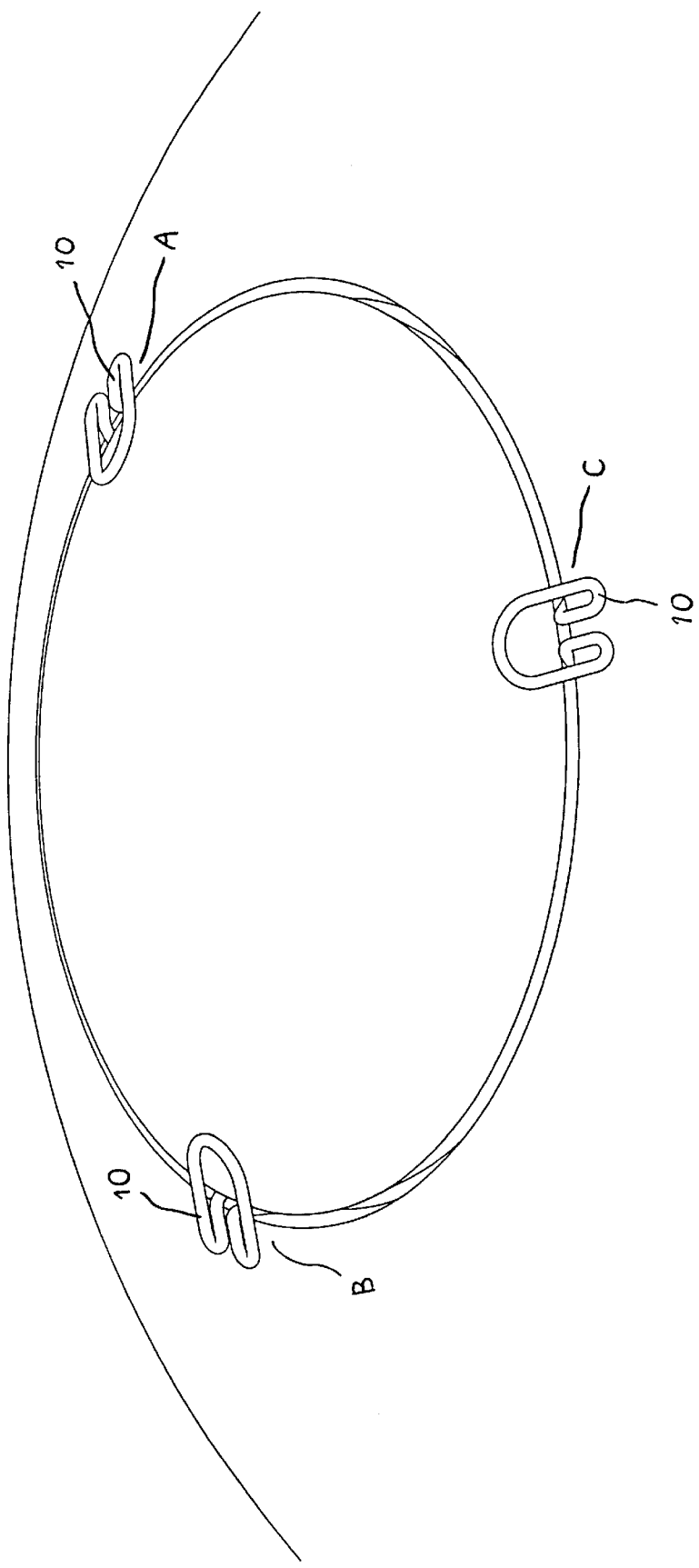

As shown in FIGS. 2a–2e, a skull 50 has an opening 52 that is left from the skull operation. The opening 52 has a cross section 54. Three fixation devices of the present invention are disposed in the positions designated as A, B, and C, as shown in FIG. 2e. FIG. 2a shows the state of the skull prior to the skull fixation. Two fixation devices are tightly retained at the A and B positions by pushing them in the directions indicated by arrows shown in FIG. 2b, wherein the clamp top portion 10 and the bottom clamp leg 30 elastically clamp the edge of the opening 52 with the clamp rod 20 abutting the cross section 54. FIG. 2c shows a cut part 60 of the skull having a cross section 62 is inserted into the opening 52 and clamped by the two fixation devices being securely retained at the A and B positions of the skull. FIG. 2d shows that the cut part 62 near the C position at the edge of the opening 52 is slightly lifted upward to allow a third fixation device to be retained at the C position at the edge of the opening 52. The third fixation device slants from the cut part 62 to the C position with one end of the clamp top portion 10 contacting the C position of the skull 50 and another end thereof contacting the cross section 62 of the cut part 60, before the lifted portion of the cut part 62 being pressed down in the direction indicated by the arrow. FIG. 2e shows the profile of the fixed skull.

In the fixation process of the present invention, no tool is used. In addition, the fixation process is simple to reduce substantially the operation duration. In view of skull fixation device of the present invention being elastic, the cut part may have a slight movement to the original skull, thereby resulting in acceleration of the post-surgical healing process.

What is claimed is:

1. A skull fixation device comprising:
   a clamp top portion;
   two clamp rods connected with said clamp top portion; and
   two bottom clamp legs each connected with a respective one of said two clamp rods;

wherein said two clamp rods are substantially coplanar and form an angle ranging between 30° and 150°, and wherein an imaginary surface is formed by the two clamp rods is substantially perpendicular to said clamp top portion;

wherein first ends of said two bottom clamp legs and first end of said clamp top portion are spaced at a first interval, second ends of said two bottom clamp legs and second end of said clamp top portion are spaced at a second interval; and wherein said first interval and said second interval are substantially equal and are on two opposite sides of said imaginary plane.

2. The skull fixation device as defined in claim 1, wherein said clamp top portion and said two clamp rods are made integrally; and wherein said two clamp rods and said two bottom clamp legs are made integrally.

3. The skull fixation device as defined in claim 2, wherein said two clamp rods and said two bottom clamp legs are made of an elastic metal wire.

4. The skull fixation device as defined in claim 1, wherein said angle ranges between 60° and 120°.

5. The skull fixation device as defined in claim 4, wherein said angle ranges between 75° and 105°.

6. The skull fixation device as defined in claim 4, wherein said two clamp rods and said two bottom clamp legs form substantially an angle of 90°.

7. The skull fixation device as defined in claim 5, wherein said two clamp rods and said two bottom clamp legs form substantially an angle of 90°.

* * * * *